United States Patent
Duggan et al.

(10) Patent No.: US 9,408,795 B2
(45) Date of Patent: Aug. 9, 2016

(54) METHOD FOR ENHANCING THE GROWTH AND FULLNESS OF HAIR

(71) Applicant: Avon Products, Inc., Suffern, NY (US)

(72) Inventors: Michele C. Duggan, Middletown, NY (US); Satish Parimoo, Bridgewater, NJ (US); Cheng S. Hwang, New Milford, NJ (US)

(73) Assignee: Avon Products Inc, New York, NY (US)

( * ) Notice: Subject to any disclaimer, the term of this patent is extended or adjusted under 35 U.S.C. 154(b) by 260 days.

(21) Appl. No.: 14/036,455

(22) Filed: Sep. 25, 2013

(65) Prior Publication Data

US 2014/0024603 A1    Jan. 23, 2014

Related U.S. Application Data

(62) Division of application No. 13/231,329, filed on Sep. 13, 2011, now Pat. No. 8,568,797.

(51) Int. Cl.
| | |
|---|---|
| *A61K 36/185* | (2006.01) |
| *A61K 8/49* | (2006.01) |
| *A61K 38/06* | (2006.01) |
| *A61K 31/045* | (2006.01) |
| *A61K 31/426* | (2006.01) |
| *A61K 45/06* | (2006.01) |
| *A61Q 7/00* | (2006.01) |
| *A61K 8/34* | (2006.01) |
| *A61K 8/97* | (2006.01) |

(52) U.S. Cl.
CPC . *A61K 8/49* (2013.01); *A61K 8/342* (2013.01); *A61K 8/97* (2013.01); *A61K 31/045* (2013.01); *A61K 31/426* (2013.01); *A61K 36/185* (2013.01); *A61K 38/06* (2013.01); *A61K 45/06* (2013.01); *A61Q 7/00* (2013.01)

(58) Field of Classification Search
None
See application file for complete search history.

(56) References Cited

U.S. PATENT DOCUMENTS

| | | |
|---|---|---|
| 7,618,662 B2 | 11/2009 | Hines et al. |
| 2003/0077614 A1 | 4/2003 | Christiano |
| 2005/0171023 A1 | 8/2005 | Cai et al. |
| 2007/0036740 A1 | 2/2007 | Reed |
| 2007/0185038 A1 | 8/2007 | Bissett et al. |
| 2008/0131389 A1* | 6/2008 | Shibuya et al. ............. 424/70.5 |
| 2009/0104295 A1 | 4/2009 | Kohno |
| 2010/0158828 A1 | 6/2010 | Ptchelintsev et al. |
| 2012/0003331 A1 | 1/2012 | Ptchelintsev |

FOREIGN PATENT DOCUMENTS

JP    2003226632 A    8/2003

OTHER PUBLICATIONS

Tsuboi R. et al. "Antisense oligonucleotide targeting fibroblast growth factor receptor (FGFR)-1 stimulates cellular activity of hair follicles in an in vitro organ culture system", International Journal of Dermatology, Wiley-Blackwell Publishing Ltd, UK, vol. 46, No. 3, Mar. 1, 2007.

* cited by examiner

*Primary Examiner* — Chris R Tate
*Assistant Examiner* — Randall Winston
(74) *Attorney, Agent, or Firm* — David M. Joyal

(57) ABSTRACT

New fibroblast growth factor receptor 1 (FGFR1) inhibitors have been identified which are useful for promoting the retention and/or growth of keratin fibers, such as hair of the scalp, hair of the face (moustache, beard, etc.), eyebrows, eyelashes, and the like. The FGFR1 inhibitors may be formulated in effective amounts in a variety of cosmetic and personal care products.

6 Claims, No Drawings

METHOD FOR ENHANCING THE GROWTH AND FULLNESS OF HAIR

This application is a divisional of, and claims priority to, U.S. patent application Ser. No. 13/231,329 filed on Sep. 13, 2011, the entirety of which is incorporated by reference herein.

FIELD OF THE INVENTION

The present invention relates generally to compositions and methods for enhancing the growth and fullness of keratin fibers, such as hair and eyelashes. More specifically, the invention relates to the use of fibroblast growth factor receptor 1 (FGFR1) inhibitors to improve the retention and/or growth of keratin fibers.

BACKGROUND OF THE INVENTION

Consumers continually seek to improve the appearance of their hair. Hair loss, slowed hair growth, and the thinning of hair are problems that afflict both men and women, and are associated with low self-esteem, lack of self-confidence, increased self-consciousness, and depression, and therefore can have a severe negative impact on general quality of life. To date, topical treatments aimed at improving hair growth and the appearance of hair have largely been ineffective. Thus, there remains a need for new hair care products that correct such deficiencies.

Keratin fiber follicles are dynamic structures that generate keratin fibers through a complex, highly regulated growth and remodeling cycle. Keratin fiber follicles follow a specific growth cycle, which includes the three distinct phases of anagen (growth phase), catagen (transitional phase), and telogen (resting phase). Each keratin fiber on the body is in its own phase of the growth process at any given time. Once the growth process is completed, a new keratin fiber will normally start the growth process over. Fibroblast growth factor receptor 1 (FGFR1) is one of a family of transmembrane fibroblast growth factor receptor tyrosine kinases, and is involved in the keratin fiber growth process.

Various approaches have attempted to prevent keratin fiber loss and thinning, and to enhance the growth, fullness, and appearance of keratin fibers, but these have been largely unsuccessful. Accordingly, there remains a need for effective keratin fiber care products that can address the problems of poor keratin fiber appearance, keratin fiber loss, slowed keratin fiber growth, and the thinning of keratin fibers.

The foregoing discussion is presented solely to provide a better understanding of the nature of the problem confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, new fibroblast growth factor receptor 1 (FGFR1) inhibitors have been identified which will be useful for promoting the retention and/or growth of keratin fibers, such as hair of the scalp, hair of the face (moustache, beard, etc.), eyebrows, eyelashes, and the like. The FGFR1 inhibitors may be formulated in effective amounts in a variety of cosmetic and personal care products.

The invention provides a method for promoting retention and/or growth of keratin fibers comprising topically applying to an area of skin containing keratin fiber follicles a composition comprising a topically acceptable vehicle and a fibroblast growth factor receptor 1 (FGFR1) inhibitor for a time sufficient to delay the transition of the keratin fiber follicle from the anagen phase to the catagen phase. The FGFR1 inhibitors of the invention include cis-6-nonenol, thiazolylalanine, or a botanical extract of *Pouzolzia pentandra*, and are usually present in the compositions in an amount from about 0.0001% to about 10% by weight. The compositions may further include an additional hair growth agent, such as 5-alpha-reductase inhibitors, vasodilators, prostaglandin F2 α analogs, microcirculation enhancers, creatine, biotinylated tri-peptides, and the like. The compositions may be in the form of a shampoo, hair conditioner, pomade, hair gel, hydroalcoholic tonic, or mousse, to name a few.

These and other aspects of the invention will be better understood by reading the following detailed description and appended claims.

DETAILED DESCRIPTION

All terms used herein are intended to have their ordinary meaning in the art unless otherwise provided. All concentrations are in terms of percentage by weight of the specified component relative to the entire weight of the composition. As used herein, the term "consisting essentially of" is intended to limit the invention to the specified materials or steps and those that do not materially affect the basic and novel characteristics of the claimed invention, as understood from a reading of this specification.

The term "keratin fiber" refers to any hair of the body, including hair of the scalp, eyelashes, hair of the face (e.g., moustache, beard, eyebrows), and the like. In preferred practice, the compositions are applied to scalp or to the hair of the scalp.

Inhibiting or reducing FGFR1 delays the transition of the keratin fiber follicle from the anagen phase to the catagen phase, thereby prolonging the amount of time that a keratin fiber follicle remains in the anagen phase. Therefore, inhibiting or reducing FGFR1 allows for increased growth of keratin fiber follicles, while delaying the shedding of the keratin fibers. Increasing the growth and retention of keratin fiber follicles leads to increased hair fullness and an improved overall appearance of hair.

The present invention is founded, in part, on the discovery that certain new FGFR1 inhibitors are useful for promoting the retention and/or growth of keratin fibers. Specifically, the FGFR1 inhibitors of the invention include botanical extracts from *Pouzolzia pentandra*, as well as cis-6-nonenol, and thiazolylalanine. Surprisingly, it has been found that applying these agents to keratin fiber follicles in an amount that is sufficient to delay the transition of the keratin fiber follicle from the anagen phase to the catagen phase, increases the growth of keratin fibers, increases the length of keratin fiber shafts, delays the shedding, or falling out of keratin fibers, and leads to increased hair fullness, health, and improved overall appearance of keratin fibers.

Non-limiting examples of improvements in keratin fibers imparted by use of the compositions of the invention comprise:

(a) improvement in root sheath thickness;
 (b) improvement in fiber anchorage;
 (c) decrease in keratin fiber loss;
 (d) reduction in keratin fiber breakage;
 (e) increase in keratin fiber strength;
 (f) improvement in keratin fiber growth rate;
 (g) improvement in shine;

(h) improvement in the number of visible keratin fibers;
(i) improvement in keratin fiber length; and/or
(j) improvement in keratin fiber volume.

The compositions useful in the methods of the invention may comprise FGFR1 inhibiting amounts of cis-6-nonenol, thiazolylalanine, and botanical extracts from *Pouzolzia pentandra*, and combinations thereof. The extracts of *Pouzolzia pentandra* may be derived from the leaf, stem, root, flower, or any other portion of the plant. The FGFR1 inhibitors may be formulated in effective amounts in a variety of cosmetic and personal care products.

*Pouzolzia* is a genus of flowering plants in the nettle family, native to regions such as Africa and India. The *Pouzolzia* species of the present invention is *Pouzolzia pentandra*, which is a perennial that grows up to 1 m tall, and is glabrous to sparsely hispid herb. The plant extract or components and/or active constituents for use in the present invention are preferably derived directly from the plant. The components may be in a pure form, a semi-pure form, or in an unpurified form. The components may be in the form of an extract obtained by aqueous or organic solvent extraction. Non-limiting examples of organic solvents that may be used in extraction include acetic acid, diethyl ether, ethyl acetate, lower alcohols (e.g., methanol, ethanol, isopropanol, butanol), dichloromethane, chloroform, hexane, benzene, toluene, xylene, and petroleum ether, and combinations thereof. The solvent may be either polar or non-polar, protic or aprotic, water-miscible or water-immiscible. The pH may be acidic, neutral, or alkaline. Well-known methods in the art may be used for aqueous or organic solvent extraction. An extraction time between about 1 to about 8 hours at a temperature between about 30° C. and about 90° C. is typically suitable. The collected extract is then typically fine-filtered to remove debris, and may be used directly, or it may be concentrated, for example, by distilling the solvent or by other conventional processing; the extract may also be provided in powder form.

Thiazolylalanine, as used herein, may be either 4-D-thiazolylalanine or 4-L-thiazolylalanine (CAS No. 119433-80-6), with 4-L-thiazolylalanine being preferred. The structure of 4-L-thiazolylalanine is shown below.

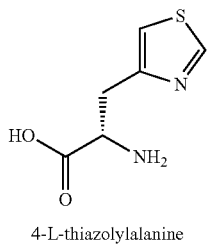 [SMILES: N[C@@H](Cc1cscn1)C(=O)O]

4-L-thiazolylalanine

4-L-thiazolylalanine is commercially available from PepTech (Burlington, Mass.) and from Synthetech (Albany, Oreg.). The synthesis of 4-L-thiazolylalanine is described in U.S. Pat. No. 5,275,950 to Dickman et al, the disclosure of which is incorporated by reference herein.

The FGFR1 inhibiting amounts of the agents of the invention may be present in the compositions in an amount that is from about 0.0001% to about 10% by weight, based on the total weight of the composition. The compositions of the invention may also comprise an amount of the FGFR1-inhibiting agent from about 0.01 weight % to about 3 weight % based on the total weight of the composition; preferably from about 0.1 weight % to about 2 weight %; and more preferably from about 0.1 weight % to about 1 weight %, based on the total weight of the composition. The composition may also comprise the FGFR1 inhibiting agent in an amount of about 0.005%, about 0.01%, about 0.05%, about 0.1%, about 0.5%, about 1%, about 2%, about 3%, about 4%, or about 5%, all percents by weight, based on the total weight of the composition.

In addition to the described FGFR1 inhibiting agents, the compositions for use in the invention may optionally comprise one or more additional agents. These additional agents can have any number of functions. The additional agents may promote keratin fiber growth. The additional agents that promote keratin fiber growth may comprise, for example, Procapil®, a combination of vitaminated biotinyl tripeptide-1 with apigenin and oleanolic acid available from Sederma, Inc., and corn extract (e.g., from International Specialty Products, Inc.), which is believed to inhibit FGFR1.

The compositions useful in the methods of the invention may also optionally comprise agents that inhibit or prevent keratin fiber follicle damage, such as tetrahyrocurcumin and extracts of *Eclipta*, both of which have been reported in the literature in the treatment of hair loss. Other agents that act to anchor and strengthen the roots of keratin fibers may optionally be included in the compositions of the invention as well.

The compositions useful in the methods of the invention may also optionally comprise agents that promote healthy keratin fiber growth. These additional agents may act to promote healthy keratin fiber growth by any number of different mechanisms. For example, corn extract is believed to impart health and a healthy appearance to keratin fibers by affecting connective tissue components and keratin fiber growth, acting directly on keratin fibers themselves. N-biotinyl-gly-his-lys is believed to affect metabolic processes involved in keratin fiber growth, thereby promoting its health and healthy appearance. N-biotinyl-gly-his-lys is a biotin complex of the tripeptide gly-his-lys, described, for example in Int. Pat. Appl. Publ. WO 00/58347, the contents of which are herein incorporated by reference. As used herein, "N-biotinyl-gly-his-lys" is used interchangeably with the terms "biotinylated tri-peptide," "biotinylated peptide," "peptide-biotin complex," "tri-peptide," and the like. Available from Sederma, Inc., Procapil® is marketed for use in reducing scalp hair loss, in particular, scalp hair loss upon aging, where it is used at a concentration of about 3 weight %.

Other agents that may be optionally added to the compositions of the invention comprise those that enhance keratin fiber thickness, such as hydrolyzed wheat protein. Wheat protein refers to one or more polypeptides extracted from wheat, and can include mixtures of wheat polypeptides and wheat oligosaccharides. The wheat protein component may include a protein/starch mixture known as "Cropeptide W," INCI name "hydrolyzed wheat protein (and) hydrolyzed wheat starch," (e.g., from Croda, Inc., Columbus, N.J.). Cropeptide W comprises a hydrolyzed wheat protein and at least partially hydrolyzed wheat oligosaccharides. The oligosaccharides are solubilized and can constitute about 2.0% to about 3.5% of the Cropeptide W mixture. Wheat proteins used in the instant invention may comprise Cropeptide W or other polypeptide/oligosaccharide mixture, having a substantially similar composition. The compositions of the instant invention may comprise an amount of wheat protein from about 0.01 weight % to about 5 weight % based on the total weight of the composition; preferably from about 0.1 weight % to about 3 weight % based on the total weight of the composition; and more preferably from about 1 weight % to about 2 weight %, or about 1.0 weight %, based on the total weight of the composition.

Other agents that may be optionally added to the compositions of the invention comprise those that act as an exfoliant, such as lactic acid. The compositions useful in the methods of the invention may also optionally comprise agents that act on stearoyl coenzyme A desaturase, such as *Eclipta*, which is believed to reduce sebum production, thereby improving the health and appearance of, for example, the scalp.

The compositions useful in the methods of the invention may also optionally comprise menthol, or other agents that cause sensation in the area to which the compositions are applied.

The compositions according to the invention may also optionally comprise one or more 5-alpha reductase inhibitors. Such compounds are known to assist in promotion of hair growth, and include, but are not limited to, saw palmetto (*Serenoa*) extract, *Emblica officianalis* extract, beta-glycyrrhetic acid, estradiol, estrone, progesterone, or azasteroids, such as finasteride or dutasteride.

The compositions according to the invention may also optionally comprise one or more vasodilators. Vasodilation has long been associated with an increase in keratin fiber growth on the scalp and on any other area of the skin where keratin fibers grow. Thus, use of one or more vasodilation agents can supplement the activity of the compounds and enhance the overall efficacy of the formulation. Examples of useful vasodilation agents include, but are not limited to, arginine, ginseng extracts, gingko extracts, swertia extracts, calpronium chloride, diphenhydramine hydrochloride, gamma-oryzanol, prostaglandins, vitamin E derivatives such as vitamin E nicotinate, pinacidil, minoxidil, phthalides, quina extracts, *Capsicum* extracts, orange peel extracts, and citron extracts The compositions according to the invention may also optionally comprise one or more microcirculation enhancers. Apigenin is a citrus-derived flavonoid believed to promote microcirculation when topically applied, and may be included in the compositions of the invention.

The compositions according to the invention may also optionally comprise prostaglandin F2 α analogs.

The compositions useful in the methods of the invention may also optionally comprise creatine. Creatine is a naturally-occurring amino acid derivative that is thought to play a role in cellular energy metabolism. Creatine is commercially available, e.g., as Cosmocair® C100 (INCI name, hydrocreatine) or TEGO® Cosmo C100, from Evonik Industries. TEGO® Cosmo C100, for example, is sold as an additive for skin and hair formulations, and is suggested for use at a concentration of from about 0.5 weight % to about 1.4 weight % based on the total weight of the composition.

The compositions useful in the methods of the invention may also optionally comprise algae extracts. An algae extract, as used herein, refers to an extract of marine algae. Preferred marine algae include, for example, *Pelvetia canaliculata* and/or *Laminara digitata*. The combination of the tri-peptide with creatine allows for much lower effective amounts of the algae extract component compared to levels at which it is conventionally used. The compositions of the instant invention may comprise an amount of algae extract from about 0.001 weight % to about 5 weight % based on the total weight of the composition; preferably from about 0.01 weight % to about 3 weight %; and more preferably from about 0.02 weight % to about 1 weight %, or about 0.020 weight %, based on the total weight of the composition.

Additionally, it is believed that the algae extract may also act to maintain healthy structure and function of keratin fiber proteins by stimulating "heat shock proteins" (HSPs). Heat shock proteins (HSPs), also known as "stress proteins," are a family of highly conserved proteins found in all organisms. HSPs are induced by a wide variety of stresses, such as increased temperature, oxygen deprivation, pH changes, chemical insult, UV radiation, and the like. These stresses modify the folding structure of proteins. Improperly folded proteins lead to loss of function and potentially cell death. HSPs bind to proteins during stress to help maintain and/or restore protein structure and function. Without wishing to be bound by theory, it is believed that the algae extract increases activity of HSP27 and HSP70 at the gene level, thereby further protecting keratin fiber proteins, especially during periods of stress. Stresses to keratin fibers may include, for example, stresses from curling the keratin fibers, heat, brushing or combing hair, and shampooing and conditioning hair. Suitable agents for modulating HSPs include, for example, *Gynostemma*, coconut water, *Azadiracta*, and *Rhodeola*, described, for example, in U.S. Published Patent Application US2005/0147578, the contents of which are herein incorporated by reference.

The compositions of the invention may optionally further comprise tocopherol. Tocopherol, or vitamin E, is known to act as an antioxidant, scavenging free radicals that can damage skin. The vitamin may be used in its active form, namely α-tocopherol, and/or as one or more of its more stable derivatives, such as its ester, tocopherol acetate and/or the form tocopheryl linoleate. Tocopherol and its devivatives are widely commercially available, e.g., tocopheryl linoleate is available from Barnet Products, Corp, N.J. The compositions can comprises an amount of tocopherol acetate from about 0.001 weight % to about 5 weight % based on the total weight of the composition; preferably from about 0.01 weight % to about 3 weight % based on the total weight of the composition; and more preferably from about 0.02 weight % to about 2 weight %, or about 0.02 weight %, based on the total weight of the composition.

The compositions of the invention may also optionally comprise one or more antioxidants, which can protect against free radicals that can contribute to keratin fiber loss, as well as protect keratin fibers from the drying effects of the sun and other photodamage. Examples of useful antioxidants include, but are not limited to ginkgo-biloba, beta carotene, green tea, ascorbic acid and derivatives thereof, such as, for example sodium ascorbyl phosphate and magnesium ascorbyl phosphate, camosic acid (rosemary), resveratrol and derivatives thereof, N-acetyl cysteine, and BHT and BHA. Green tea, as well as other antioxidants, may be in the form of an extract or any other known form of the antioxidant, as well as the active components of extracts, e.g., catechin based flavonoids such as EGCG (epigallcatechin gallate) from green tea, rosemary extract, and the like. Antioxidants, if used, will be present in an amount of from about 0.0001 to about 10%, based on the total weight of the composition.

The composition of the invention may optionally further comprise one or more cell differentiation activators. Examples of such agents are extracts of sage, for example clary sage, and/or any differentiation-active compounds, such as sclareolide, obtainable therefrom. Other examples of useful differentiation active compounds are forskolin, 7-dehydrocholesterol, and Vitamin D3 analogs. Specifically, a clary sage fermented extract is commercially available from Avoca/RJ Reynolds. Amounts used in the compositions of the invention may be from about 0.001 to about 10%, preferably from about 0.01 to about 1%, based on the total weight of the composition.

The compositions of the invention may also optionally comprise one or more firming components, which promote the support in the basement membrane and dermis to encourage and support the keratin fiber structure. Examples of firming components are compounds that enhance the amount of collagen and/or elastin in the skin, for example, collagenase and or elastase inhibitors, or collagen or elastin synthesis enhancers. Such compounds include, but are not limited to triterpenoid-containing extracts and refined compounds, for example, white birch bark extract, silver birch bark extract, *Boswellia* extract, bearberry extract, *Centella asiatica* extract, *Mimosa tenuiflora* bark extract, or *Pygeum* (*Prunus*) *africanum* extract and individual active compounds that may be present in these extracts, including betulinol (betulin), betulinic acid, boswellic acid, ursolic acid, oleanolic acid, oleanol, asiaticoside, asiatic acid, and madagassic acid; phenolic-containing extracts, such as green tea extracts and apple extracts, and compounds contained therein, such as EGCG, ECG, catechins, phenylpropanoids, and phloretin; and Vitamin C and derivatives thereof for enhancing collagen synthesis. A preferred collagenase inhibitor is *Mimosa tenuiflora* extract known as tepescohuite, and a preferred Vitamin C derivative is BV-OSV. The firming agents may be used in the compositions of the invention in the amount of about 0.001 to about 10% based on the total weight of the composition.

The compounds for use in the invention are used in the form of a topical formulation for application to any area of the body that contains keratin fiber follicles. The vehicle in which the active ingredients are applied can be in any form typically used for application to keratin fibers. The compositions of the invention may be applied to keratin fibers that are either wet or dry.

The compositions will typically include a topically acceptable vehicle, by which is meant a diluent, solvent, or carrier that is generally safe and non-irritating when applied to a human integument, in particular, for application to hair or scalp.

It is contemplated that any cosmetically acceptable vehicle known in the art will be useful. The vehicle may comprise water and/or hydrophobic and/or hydrophilic organic solvents. Suitable hydrophilic solvents include but are not limited to, alcohols and polyols (e.g., ethanol, isopropanol, propanol, butanol, benzyl alcohol, phenylethyl alcohol, propylene glycol, butylene glycol, pentylene glycol, hexylene glycol, caprylyl glycol, glycerin, etc.), carbitol, glycol ethers such as, for example, ethylene glycol monobutyl ether, propylene glycol monomethyl ether, propylene glycol monobutyl ether, dipropylene glycol and diethylene glycol alkyl ethers such as, for example, diethylene glycol monoethyl ether or monobutyl ether, and any combinations thereof. Water is a preferred vehicle component.

Typically, the amount of water in the vehicle is about 5% to about 100%, more typically from about 20% to about 99% by weight, and preferably, from about 50% to about 97% by weight. The vehicle may also comprise a hydroalcoholic solution, which includes an amount of a lower alcohol (e.g., ethanol, isopropanol, etc.) in combination with water. For example, the vehicle may comprise from about 20% to about 99% by weight water, and from about 1% to about 80% by weight alcohol, typically ethanol or isopropanol.

The vehicle may also be in the form of an emulsion. Emulsions include oil-in-water, silicone-in-water, water-in-oil, water-in-silicone, and the like. When formulated as an emulsion, an emulsifier is typically included.

The compositions may be applied as a shampoo, a hair rinse, a hair conditioner, a pomade, a hair gel, a mousse, a hydroalcoholic tonic, a cream, a spray, an emulsion, a liquid, or any other form that is normally used for treatment of keratin fibers.

The composition may also comprise materials that are useful in improving the condition of keratin fibers or the area to which the compositions are applied, such as the scalp, for example, or which impart other useful functions, including moisturizers, detanglers, thickeners, gelling agents, film formers, fragrance, preservatives, chelating agents, pH adjusters, and the like.

Suitable other ingredients that may be optionally included in the compositions of the invention include, but are not limited to, amino acids, antioxidants, colorants, emollients, emulsifiers, excipients, fillers, humectants, minerals, photostabilizing agents (e.g., UV absorbers), stabilizers, staining agents, surfactants, viscosity and/or rheology modifiers, vitamins, waxes and mixtures thereof. It is contemplated that the compositions of the present invention can also include anti-dandruff, deodorant, sunscreen and/or antiperspirant ingredients.

The compositions may optionally further comprise any number of customary additives, depending on the area of the body to which the compositions are applied. For example, the compositions may comprise one or more skin benefiting agents selected from the group consisting of salicylic acid; alpha hydroxyl acids, such as but not limited to glycolic acid and lactic acid; thiodipropionic acid; amino acids; peptides and botanical extracts to name a few. In one preferred embodiment, the composition may comprise salicylic acid, which helps to prevent acne and blackheads from forming. The one or more skin benefiting agents may be present in the composition in an amount from about 0.001% to about 5%, preferably from about 0.01% to about 2.5%, and more preferably from about 0.1% to about 1%, based on the total weight of the composition.

Frequency of application of the compositions to the desired area of keratin fiber follicles may occur at least once a week. The compositions of the invention may also be applied three to five times a week, or, preferably, they may be applied daily. The compounds of the invention may be applied once daily, twice daily, three times daily, four times daily, five times daily, or more, as needed to obtain the desired result.

The timing of its usage will be determined according to the cause of the keratin fiber loss, thinning, or poor appearance; a temporary keratin fiber loss, due for example to drug exposure, may require only regular use on a temporary basis, until after the removal of the harmful stimulus and subsequent re-growth of hair to a satisfactory level. However, for pattern or age-related baldness or thinning keratin fibers, where the causative agent is a constant presence, a chronic application is preferred, e.g., the application will be regularly applied over the lifetime of the user. The period of topical application may be over the lifetime of the user, preferably for a period of at least about one week to about eight weeks, more preferably from about three months to about twenty years, more preferably from about six months to about ten years, more preferably still from about one year to about five years, or for as long as the user is interested in treating his or her keratin fibers. The period of topical application may also be from about two months to about three months, about three months to about one year, or from about one month to about two years. The amount of product applied will vary according to the form of the product, but will normally be in accordance with the industry accepted methodology for the use of a product of the same type. A representative application procedure will involve application of the formulation to the area in need of treatment once or twice a day, and leaving the formulation in place for a period of between several minutes to several hours.

Example 1

Representative formulations of FGFR1-inhibiting compositions according to the invention are provided in Table 1.

TABLE 1

| Material | Amount (wt %) | Amount (wt %) |
|---|---|---|
| *Pouzolzia pentandra* | 0.0001-5% | 0.01 |
| Tetrahydrocurcumin | 0-5% | 0.01 |
| *Eclipta* | 0-5% | 0.01 |
| Procapil ® | 0-5% | 0.1 |
| Corn extract | 0-5% | 0.1 |
| Hydrolyzed wheat protein | 0-10% | 1.0 |
| Exfoliant (e.g., Lactic acid) | 0-10% | 2 |
| Sensate (e.g., Menthol) | 0-5% | 0.3 |
| Water/ethanol | q.s. | q.s. |

Example 2

The following Example demonstrates the results of an assay to determine the ability of candidate agents to inhibit FGFR1 gene expression.

Method: PCR to assess FGFR1 gene expression in human dermal papilla cells, following administration of L-4-Thiazolylalanine, *Pouzolzia petandra*, or cis-6-nonenol.

Human dermal papilla cells (Cell Applications, CA) were plated at 5000 cells/cm$^2$ in collagen-coated 6-well culture plates in the Papilla Cell Growth Medium (Cell Application, CA) overnight in humidified atmosphere of 5% $CO_2$ at 37° C. When dermal papilla cells reached 80-90% confluence, the medium was replaced with fresh medium and the compounds (L-4-Thiazolylalanine, *Pouzolzia petandra*, or cis-6-nonenol) dissolved in DMSO were added to the wells in duplicate at a concentration of 0.002% or 0.001%. DMSO was used a vehicle control. Following 48-hour incubation, the medium was removed and the cells were collected in the Lysis/Binding Solution (Ambion, Tex.) after being washed with cold PBS.

Total RNA was extracted from dermal papilla cells by using the RNAqueous kit (Ambion, Tex.) according to the manufacture's instruction. RNA was quantified on the Nanodrop ND-1000 Spectrophotometer (NanoDrop Technologies, DE) and the confirmation of integrity was determined using the Agilent Bioanalyzer before RNA was further processed for cDNA preparation. Reverse transcription was carried out on 3 μg of total RNA using the ABI High capacity cDNA Reverse Transcription kit (Perkin-Elmer Applied Biosystems Inc., CA) according to manufacturer's instructions. Parameters for the reverse transcription: 25° C., 10 minutes; 37° C., 2 hours; 85° C., 5 minutes.

RNA abundance of FGFR1 was measured using quantitative Real-Time PCR. 18S rRNA was used as the internal control. Gene expression was performed by using human specific TaqMan primers for the FGFR1 gene (Applied Biosystems cat number HS0024111_ml) and 18S gene (Applied Biosystems cat number HS99999901_sl). PCR was performed on an Applied Biosystems ABI 7900 Real Time PCR system (Perkin-Elmer Applied Biosystems Inc., CA) under the following conditions: 50° C., 2 minutes for 1 cycle; 95° C., 10 minutes for 1 cycle; 95° C., 15 seconds and 60° C., 1 minute for 40 cycles. All samples were run in triplicate and normalized to 18S and expressed as a percentage of the control.

Results: The percent inhibition of FGFR1 gene expression following administration of L-4-Thiazolylalanine, *Pouzolzia petandra*, or cis-6-nonenol is presented in Table 2.

TABLE 2

| FGFR1 Inhibitor | Concentration (w/v) | Percent Inhibition of FGFR1 Expression |
|---|---|---|
| L-4-Thiazolylalanine | 0.001% | 59.13% |
| *Pouzolzia petandra* | 0.002% | 43.37% |
| cis-6-nonenol | 0.002% | 28.25% |

The invention having been described by the forgoing description of the preferred embodiment, it will be understood that the skilled artisan may make modifications and variations of these embodiments without departing from the spirit or scope of the invention as set forth in the following claims.

All patent and non-patent literature discussed above is hereby incorporated by reference in its entirety for all purposes.

We claim:

1. A method for promoting growth of keratin fibers in the skin of a subject in need thereof comprising topically applying to said skin a composition comprising a topically acceptable vehicle and a fibroblast growth factor receptor 1 (FGFR 1)-inhibiting amount of cis-6-nonenol, at least once daily, for a period of at least one week, wherein the transition of the keratin fiber follicles from the anagen phase to the catagen phase is delayed.

2. The method according to claim 1, wherein said FGFR 1-inhibiting amount is from about 0.0001% to about 10% by weight of said composition.

3. The method according to claim 1, wherein said composition further includes an additional hair growth agent selected from the group consisting of 5-alpha-reductase inhibitor, vasodilators, prostaglandin F2 α analogs, microcirculation enhancers, creatine, biotinylated tri-peptide, and combinations thereof.

4. The method according to claim 1, wherein said composition is in the form of a shampoo, hair conditioner, pomade, hair gel, hydroalcoholic tonic, or mousse.

5. The method according to claim 1, wherein said composition is applied to the hair for at least two weeks.

6. The method according to claim 5, wherein said FGR1-inhibiting amount is from about 0.001% to about 3% by weight of said composition.

* * * * *